United States Patent [19]

Yoshida et al.

[11] 4,198,393

[45] Apr. 15, 1980

[54] CYCLIC ACETALS OF 2-METHYL-2-PENTENAL AND FOOD FLAVOR USES THEREOF

[75] Inventors: Takao Yoshida, West Long Branch; Manfred H. Vock, Locust, both of N.J.

[73] Assignee: International Flavors & Fragrances Inc., New York, N.Y.

[21] Appl. No.: 19,927

[22] Filed: Mar. 12, 1979

Related U.S. Application Data

[62] Division of Ser. No. 939,911, Sep. 5, 1978, which is a division of Ser. No. 827,253, Aug. 24, 1977.

[51] Int. Cl.² ............................................... A61K 7/16
[52] U.S. Cl. ...................................................... 424/49
[58] Field of Search ................................. 424/49–58

[56] References Cited

U.S. PATENT DOCUMENTS

| | | | |
|---|---|---|---|
| 3,879,425 | 4/1975 | Hall et al. | 426/536 X |
| 3,883,558 | 5/1975 | Lamparsky | 426/536 X |
| 3,908,023 | 9/1975 | Schreiber et al. | 426/536 |
| 3,914,451 | 10/1975 | Schreiber et al. | 252/522 X |
| 3,928,644 | 12/1975 | Schreiber et al. | 426/536 X |
| 3,959,185 | 5/1976 | Barello et al. | 426/536 X |
| 3,959,396 | 5/1976 | Ochsner et al. | 252/522 X |
| 3,988,487 | 10/1976 | Sanderson et al. | 252/522 X |
| 4,036,886 | 7/1977 | Schreiber et al. | 426/536 X |

FOREIGN PATENT DOCUMENTS

| | | | |
|---|---|---|---|
| 2108567 | 10/1971 | Fed. Rep. of Germany | 260/340.9 R |
| 1453991 | 8/1966 | France | |
| 4493M | 10/1966 | France | 260/340.9 R |
| 739022 | 10/1955 | United Kingdom | 260/340.9 R |
| 1301423 | 12/1972 | United Kingdom | |

OTHER PUBLICATIONS

Hibbert et al., J. Chem. Soc. 51 (1929), pp. 611–614; Beilstein, vol. E, CCXIX:16:5(2).
Chem. Abstracts 67: 2765k (1967); 62: 11055e (1965); 78: 58492 (1973).
Fed. Register 31: 7563, May 26, 1966.

*Primary Examiner*—Shep K. Rose
*Attorney, Agent, or Firm*—Arthur L. Liberman; Franklin D. Wolffe

[57] ABSTRACT

Processes and compositions are described for the use in foodstuff, chewing gum, toothpaste and medicinal product flavor and aroma augmenting, modifying, enhancing and imparting compositions and as foodstuffs, chewing gum, toothpaste and medicinal product aroma imparting materials of cyclic acetals of 2-methyl-2-pentenal having the generic structure:

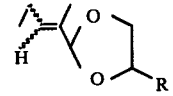

wherein R represents either hydrogen or methyl and the wavy lines signify that the cyclic acetal moiety is in either a "cis" or "trans" configuration with respect to the ethyl moiety bonded to the ethylenic moiety of the molecule. Addition of one or more cyclic acetals of 2-methyl-2-pentenal to foodstuffs, chewing gums, toothpastes and/or medicinal products produces sweet, fruity, gooseberry, green, aniseed, licorice, floral and herbal aroma characteristics and sweet, fruity, gooseberry, green, spearmint-like, aniseed, licorice, floral and herbal flavor characteristics with albedo-like flavor nuances.

1 Claim, No Drawings

CYCLIC ACETALS OF 2-METHYL-2-PENTENAL AND FOOD FLAVOR USES THEREOF

This is a divisional of application Ser. No. 939,911, filed Sept. 5, 1978, which, in turn, is a divisional application of pending prior application Ser. No. 827,253, filed Aug. 24, 1977.

BACKGROUND OF THE INVENTION

The present invention relates to cyclic acetals of 2-methyl-2-pentenal and novel compositions using such cyclic acetals of 2-methyl-2-pentenal to alter, modify, augment or enhance the flavor and/or aroma of foodstuffs, medicinal products, toothpastes, or chewing gum or impart flavor and/or aroma to said foodstuffs, medicinal products, toothpastes or chewing gum.

There has been considerable work performed relating to substances which can be used to impart (modify, augment or enhance) flavors to (or in) foodstuffs, medicinal products, toothpastes and/or chewing gum. These substances are used to diminish the use of natural materials, some of which may be in short supply and to provide more uniform properties in the finished product.

Sweet, fruity, gooseberry, green, aniseed, licorice, floral and herbal aroma characteristics and sweet, fruity, gooseberry, green, spearmint, aniseed, licorice, floral, and herbal flavor characteristics with albedo-like flavor nuances are particularly desirable for uses in many foodstuff flavors, chewing gum flavors, toothpaste flavors and medicinal product flavors.

Cyclic acetals of unsaturated aldehydes, wherein the cyclic acetal contains a five membered acetal moiety are known in the prior art. However, the use flavor uses of the cyclic acetals of our invention and one of the cyclic acetals of our invention (wherein R is methyl) have been heretofore unknown.

U.S. Pat. No. 3,760,303 (1971) discloses the cyclic acetal of 2,4-hexadienal with ethylene glycol and discloses its use in the bouquet of citrus-type odorant formulations. This compound has the structure:

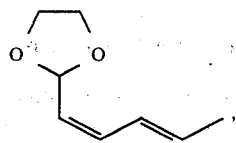

Netherlands published application No. 6,406,295 (1965) discloses gamma, delta-unsaturated aldehyde derivatives for use as perfumes, for example in soaps. These derivatives are cyclic acetals and have the structures:

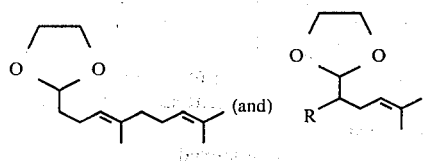

wherein R is hydrogen or methyl.

German Offenlegungschrift No. 2,103,567 (1971) discloses the use as perfumes of 2-(1-alkyl-2-alkenyl)-1,3-dioxolanes having the structure:

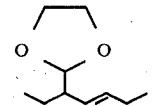

In the Federal Register 31, 7563 (May 26, 1966) and in Chem. Abstracts 62, 11055e the compound having the structure:

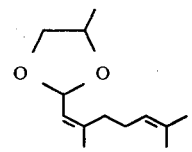

is disclosed to be useful as a synthetic food flavoring substance.

Beilstein Vol. E CCXIX at page 16:5(2) discloses 2-(1-methyl-1-butenyl)1,3-dioxolane having the structure:

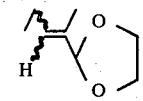

The Beilstein Abstract summarizes the article by Hibbert et al J. Chem. Soc. 51 (1929) page 611 (Title: "Studies on Reactions Relating to Carbohydrates and Polysaccharides. XX. Comparison of Tendencies of Saturated and Unsaturated Aldehydes Toward Cyclic Acetal Formation"). This compound is shown to be prepared by reacting alpha methyl beta ethyl acrolein with ethylene glycol using a 40% sulfuric acid catalyst. The compound is indicated to have a boiling point of 170°–174° C. at 12 mm Hg pressure.

2-(1-ethyl-1-pentenal)-1,3-dioxolane and 2-(1-propenyl)-4-methyl-1,3-dioxolane are shown to be prepared by Heywood and Phillips, J. Org. Chem. 25 (1960) page 1699 entitled: "The Oxidation of Unsaturated Acetals and Acylals With Peracetic Acid".

None of the foregoing references discloses or implies the subject matter of the instant invention.

THE INVENTION

It has now been discovered that novel solid and liquid foodstuff, chewing gum, medicinal product and toothpaste compositions and flavoring compositions therefor having sweet, fruity, gooseberry, green, aniseed, licorice, floral and herbal aroma characteristics and sweet, fruity, gooseberry, green, spearmint, aniseed, licorice, floral and herbal flavor characteristics with albedo-like nuances may be provided by the utilization of cyclic acetals of 2-methyl-2-pentenal having the generic structure:

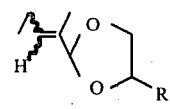

wherein R is selected from the group consisting of hydrogen and methyl and the wavy lines represent covalent bonds, and signify a "cis" or "trans" configuration of the dioxolane moiety with respect to the ethyl moiety; each moiety being bonded to the ethenyl group of the molecule.

The compounds wherein R is methyl are novel compounds. These compounds have the structures represented as follows:

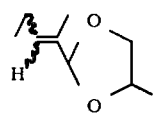
(mixture of "cis" and "trans" isomers)

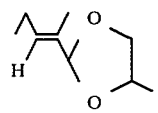
("trans" isomer)

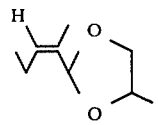
("cis" isomer)

The 2-Methyl-2-pentenal-1,2-propylene glycol acetal cis-trans isomer mixture represented by the structure:

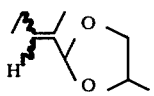

indicated as being useful, supra, may be produced preferably by reacting propylene glycol with 2-methyl-2-pentenal in the presence of an inert solvent such as cyclohexane or toluene and an acid catalyst such as paratoluene sulfonic acid or citric acid.

The reaction is carried out at reflux conditions and water produced from reaction is removed azeotropically. The time of reaction is a function of the solvent used which solvent will determine the rate of take-off of water from reaction. Thus, when using toluene, 250 grams of toluene will remove about 50 grams of water when two moles of 2-methyl-2-pentenal is reacted with 2 moles of 1,2-propanediol in a period of 11 hours. When using cyclohexane (300 ml) and 2 moles of 2-methyl-2-pentenal and 2 moles of propanediol, 54 g of water is removed in a period of 7 hours.

Preferably, the mole ratio of glycol, e.g. ethylene glycol or propylene glycol: aldehyde, 2-methyl-2-pentenal, is about 1:1. Either reactant may be used in excess. However, additional recovery problems are encountered when one of the reactants is used in excess.

At the end of the reaction time, the reaction mass is fractionally distilled yielding the product which is primarily a compound having one of the structures:

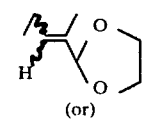
(or)
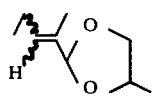

each of which structures represents a mixture of "cis" and "trans" isomers. These "cis" and "trans" isomers may be separated by preparative GLC techniques well known to those having ordinary skill in the art.

From a commercial standpoint it is most preferable to use the "cis" - "trans" isomer mixtures "as-is" rather than go through the costly GLC separation of these isomers. The "cis" - "trans" isomer mixtures of our invention have the following organoleptic properties insofar as there foodstuff flavorant use is concerned:

| Compound Name | Compound Structure | Organoleptic Properties |
|---|---|---|
| 2-(1-methyl-1-butenyl) 4-methyl-1,3-dioxolane | 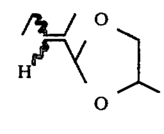 | Sweet, aniseed, licorice, green, floral and herbal aroma characteristics and sweet, aniseed, licorice, green, floral and herbal flavor characteristics with albedo-like nuance. |
| 2-(1-methyl-1-butenyl) 1,3-dioxolane | 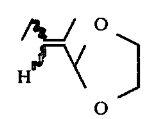 | Sweet, fruity, gooseberry and green aroma characteristics with sweet, fruity, gooseberry, green and spearmint flavor characteristics. |

As used herein in regard to flavors, the terms "alter", "modify" and "augment" in their various forms mean "supplying or imparting flavor character or note to otherwise bland, relatively tasteless substances or augmenting the existing flavor characteristics where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, mouthwashes, cough drops, aspirin and chewable medicinal tablets.

As used herein, the term "toothpaste" includes both solids and liquids useful in cleaning teeth. Toothpastes may comprise four groups of additives:

Group A: Glycerine; distilled water; sodium benzoate; if desired, artificial sweetner such as sodium saccharin and, if desired, stannous fluoride.

Group B: A basic pH buffer such as calcium carbonate and/or dicalcium phosphate.

Group C: A foaming agent such as sodium n-lauroyl sarcosinate.

Group D: A flavor material.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the cyclic acetals of 2-methyl-2-pentenal of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, acetoin and acetals (e.g., 1,1-diethoxyethane, 1,1-dimethoxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with the cyclic acetals of 2-methyl-2-pentenal of our invention by not covering or spoiling the organoleptic properties (aroma and/or taste) thereof; (ii) be non-reactive with the cyclic acetals of 2-methyl-2-pentenal of our invention and (iii) be capable of providing an environment in which the cyclic acetals of 2-methyl-2-pentenal can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of cyclic acetals of 2-methyl-2-pentenal employed in a particular instance can vary over a relatively wide range, depending upon the desired organoleptic effects to be achieved. Thus, correspondingly, greater amounts would be necessary in those instances wherein the ultimate food composition to be flavored (e.g. with a spice flavor or a specific black pepper-like flavor) is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing fum per se, medicinal product per se, toothpaste per se, or flavoring composition.

The use of insufficient quantities of cyclic acetal or mixture of cyclic acetals of 2-methyl-2-pentenal will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of cyclic acetals of 2-methyl-2-pentenal ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the cyclic acetals of 2-methyl-2-pentenal is added to the foodstuff as an integral component of a flavoring composition, it is, of course, essential that the total quantity of flavoring composition employed be sufficient to yield an effective cyclic acetal of 2-methyl-2-pentenal concentration in the foodstuff product.

Food flavoring compositions prepared in accordance with the present invention preferably contain one or more cyclic acetal(s) of 2-methyl-2-pentenal in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the cycic acetals of 2-methyl-2-pentenal with, for example, gum arabic, gum tragacanth, carrageenan and the like, and thereafter spray-drying the resultant mixture whereby to obtain the particular solid product. Pre-prepared flavor mixes in powder form, e.g., a fruit flavored powder mix are obtained by mixing the dried solid components, e.g., starch, sugar and the like and cycic acetals of 2-methyl-2-pentenal in a dry blender until the requisite degree of uniformity is achieved.

It is presently preferred to combine with the cyclic acetals of 2-methyl-2-pentenal of our invention, the following adjuvants:
Clove Oil;
Oil of Cubeb;
Phellandrene;
Oil of Coriander;
Cardamon Oil;
Spearmint Oil;
Anethole;
Oil of Pimento Leaf;
Oil of Patchouli;
Alpha-Pinene;
Beta-Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg; and
Peppermint Oil The following examples serve to illustrate the utility and process for preparing the cyclic acetals of 2-methyl-2-pentenal of our invention. It will be understood that these examples are illustrative and the invention is to be considered restricted thereto only as indicated in the appended claims.

All parts and percentages given herein are by weight unless otherwise specified.

EXAMPLE I

Preparation of
2-(1-Methyl-1-Butenyl)-4-Methyl-1,3-Dioxolane
Reaction

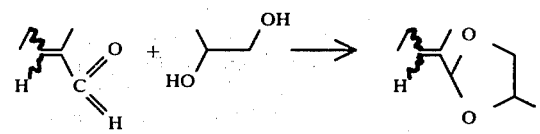

In a 2 liter reaction flask fitted with a Dean-Stark apparatus are charged 2-methyl-2-pentenal (490 g), 1,2-propandiol (380 g), citric acid (25 g) and toluene (625 g). The mixture is heated under reflux to remove water azeotropically (143 mls of water is collected) over a period of 16 hours. To this reaction mixture is added solid caustic soda flake (16 g), and the reaction mixture is stirred for 2 hours at room temperature. The crude product having a boiling point of 70–85° C. at 15 mm Hg pressure is distilled directly from the reaction flask after removing toluene at 141 mm Hg pressure. Redistillation of the crude gives 527 g (66% yield) of 98% pure product with a boiling point of 75°–79° C. at 15 mm Hg.

IR: 850 (olefin) cm$^{-1}$, 1040–1120 (ether) cm$^{-1}$, and 1670 (olefin) cm$^{-1}$, NMR: δ 0.98 (triplet, J=8Hz, C$\underline{H}_3$—CH$_2$—), 1.26 and 1.32 (two doublets,

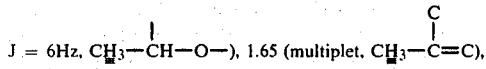

J = 6Hz, C$\underline{H}_3$—CH—O—), 1.65 (multiplet, C$\underline{H}_3$—C=C), 2.10 (quintet, J=8Hz, —C$\underline{H}_2$—CH$_3$), 3.35–3.55 and 3.95–4.40 (multiplets, —O—C$\underline{H}_2$—C$\underline{H}$—O—), 5.20 (doublet, J = 10Hz,

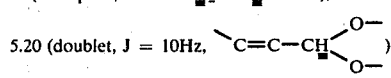

), 5.65 (broad triplet, J=8Hz, —CH—C—) ppm, mass spectrum; M/e=156, 127, 69, 41, 87, 59, 97, 141.

EXAMPLE II

Flavor Formulation

The following basic flavor formulation is prepared:

| Ingredients | Parts by Weight |
| --- | --- |
| Clove Oil | 1.0 |
| Cardamon Oil | 0.1 |
| Spearmint Oil | 5.0 |
| Anethol | 10.0 |
| Peppermint Oil, Redistilled | 83.9 |

A second formulation is prepared wherein 80% of the anethol is replaced with an equal weight of 2-(1-methyl-1-butenyl)-4-methyl-1,3-dioxolane prepared according the Example I. Both the first and the second formulation are compared in water at the rate of 10 ppm and evaluated by a bench panel of experienced tasters. It is unaminously agreed upon by the bench panel that the flavor containing the 2-(1-methyl-1-butenyl)-4-methyl-1,3-dioxolane has a more licorice/herbal note in addition to the sweet anis note, which is present in both of the flavors. The flavor containing the 2-(1-methyl-1-butenyl)-4-methyl-1,3-dioxolane also has an etheral extended refreshing effect not present in this intensity in the basic formulation which does not contain said dioxolane. This demonstrates that the compound, 2-(1-methyl-1-butenyl)-4-methyl-1,3-dioxolane does not only have sweet anis and licorice notes but also the additional etheral effect.

EXAMPLE IIIA

Flavor Preparation

The following flavor formulation is prepared by admixing the ingredients in the proportions set forth below:

| Ingredients | Parts by Weight |
| --- | --- |
| Clove Oil | 1.0 |
| Cardamon Oil | 0.1 |
| Spearmint Oil | 5.0 |
| Anethol | 2.0 |
| 2-(1-methyl-1-butenyl)-4-methyl-1,3-dioxolane prepared according to Example I | 8.0 |
| Peppermint Oil, Redistilled | 83.9 |

EXAMPLE IIIB 10 parts by weight of 50 Bloom pigskin gelatin is added to 90 parts by weight of water at a temperature of 150° F. The mixture is agitated until the gelatin completely dissolves and the solution is cooled to 120° F. 20 parts by weight of the flavor of part A supra is added to the solution which is then homogenized to form an emulsion, having a particle size typically in the range of 2–5 microns. The material is kept at 120° F. under which conditions the gelatin will not gel.

Coacervation is induced by adding, slowly and uniformly 40 parts by weight of a 20% aqueous solution of sodium sulphate. During coacervation, the gelatin molecules are deposited uniformly about each oil droplet as a nucleus.

Gelation is effected by pouring the heated coacervate mixture into 1,000 parts by weight of a 7% aqueous solution of sodium sulphate at 65° F. The resulting jelled coacervate may be filtered and washed with water at temperatures below the melting point of jelatin, to remove the salt.

Hardening of the filtered cake, in this example, is effected by washing with 200 parts by weight of 37% solution of formaldehyde in water. The cake is then washed to remove residual formaldehyde.

EXAMPLE IIIC

The following mixture is prepared:

| Ingredients | Parts by Weight |
| --- | --- |
| Liquid Flavor Composition of Part A, supra | 48.4 |
| Cab-O-Sil M-5 (Brand of Silica produced by the Cabot Corporation of 125 High Street, Boston, Mass. 02110; Physical Properties: Surface Area: 200m$^2$/gm, Nominal Particle Size: 0.012 microns Density: 2.3/lbs/cu.ft. | 3.2 |

The Cab-O-Sil is dispersed in the liquid flavor composition of Part A with vigorous stirring thereby resulting in a viscous liquid. 48.4 parts by weight of the powder flavor composition produced according to Part B, supra is then blended into said viscous liquid with stirring at 25° C. for a period of 30 minutes resulting in a thixotropic sustained release licorice flavored toothpaste.

EXAMPLE IV

Chewing Gum 100 parts by weight of chicle are mixed with 4 parts by weight of the flavor prepared in accordance with Example III. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting licorice flavor.

EXAMPLE V

Toothpaste Formulation

The following separate groups of ingredients are prepared:

| Ingredient | Parts by Weight |
|---|---|
| Group "A" | |
| Glycerin | 30.200 |
| Distilled Water | 15.325 |
| Sodium Benzoate | .100 |
| Saccharin Sodium | .125 |
| Stannous Fluoride | .400 |
| Group "B" | |
| Calcium Carbonate | 12.500 |
| Dicalcium Phosphate (Dihydrate) | 37.200 |
| Group "C" | |
| Sodium N-Lauroyl Sarcosinate (foaming agent) | 2.000 |
| Group "D" | |
| Flavor Material of Example III | 1.200 |
| Total: | 100.00 |

Procedure:

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant licorice flavor of constant strong intensity throughout said procedure (1-1.5 minutes).

EXAMPLE VI

Chewing Tobacco

Onto 100 pounds of tobacco for chewing (85% Wisc. leaf and 15% Pa. leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example III | 0.4 |

The resultant product is redried to a moisture content of 20%. On chewing, this tobacco has an excellent substantially consistent, long-lasting licorice (20 minutes) nuance in conjunction with the main fruity tobacco note.

What is claimed is:

1. A toothpaste comprising a toothpaste base and having intimately admixed therewith a formulation capable of augmenting or enhancing the organoleptic properties of aroma or taste of said toothpaste base comprising (i) from about 0.1% up to about 15% by weight based on the total weight of said flavoring composition of a cyclic acetal of 2-methyl-2-pentenal having the structure:

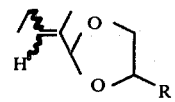

wherein R is methyl and the wavy lines represent a "cis" or "trans" configuration around the carbon-carbon double bond of said compound of the ethyl moiety with respect to the dioxolane moiety and said compound incorporating in said toothpaste base the following organoleptic properties:

| Compound Name | Compound Structure | Organoleptic Properties |
|---|---|---|
| 2-(1-methyl-1-butenyl) 4-methyl-1,3-dioxolane | | Sweet, aniseed, licorice, green, floral and herbal aroma characteristics and sweet, aniseed, licorice, green, floral and herbal flavor characteristics with albedo-like nuance. | and (ii) the remainder of said composition being a material selected from the group consisting of:
Oil of Cubeb;
Phellandrene;
Oil of Coriander;
Clove Oil;
Cardamon Oil;
Spearmint Oil;
Anethole;
Peppermint Oil;
Oil of Pimento leaf;
Oil of Patchouli;
Alpha-Pinene;
Beta-Pinene;
Beta-caryophyllene;
Dihydrocarveol;
Piperonal;
Piperine;
Chavicine;
Piperidine;
Oil of Black Pepper;
Black Pepper Oleoresin;
Capsicum; and
Oil of Nutmeg.

* * * * *